(12) United States Patent
Kawaguchi

(10) Patent No.: US 11,287,370 B2
(45) Date of Patent: Mar. 29, 2022

(54) METHOD AND DEVICE FOR ANALYZING GAS

(71) Applicant: Kanto Denka Kogyo Co., Ltd., Tokyo (JP)

(72) Inventor: Shinichi Kawaguchi, Shibukawa (JP)

(73) Assignee: Kanto Denka Kogyo Co., Ltd., Tokyo (JP)

( * ) Notice: Subject to any disclaimer, the term of this patent is extended or adjusted under 35 U.S.C. 154(b) by 0 days.

(21) Appl. No.: 16/975,274

(22) PCT Filed: Mar. 5, 2019

(86) PCT No.: PCT/JP2019/008490
§ 371 (c)(1),
(2) Date: Aug. 24, 2020

(87) PCT Pub. No.: WO2019/176624
PCT Pub. Date: Sep. 19, 2019

(65) Prior Publication Data
US 2020/0393368 A1 Dec. 17, 2020

(30) Foreign Application Priority Data
Mar. 12, 2018 (JP) .............................. JP2018-044495

(51) Int. Cl.
*G01N 21/3504* (2014.01)
*G01N 33/00* (2006.01)
*G01N 21/35* (2014.01)

(52) U.S. Cl.
CPC ..... *G01N 21/3504* (2013.01); *G01N 33/0036* (2013.01); *G01N 2021/3595* (2013.01); *G01N 2201/0636* (2013.01)

(58) Field of Classification Search
CPC ........... G01N 21/3504; G01N 33/0036; G01N 2021/3595; G01N 2201/0636
See application file for complete search history.

(56) References Cited

U.S. PATENT DOCUMENTS 7,079,252 B1 7/2006 Debreczeny et al.
2002/0051132 A1 5/2002 Ohno et al.
(Continued)

FOREIGN PATENT DOCUMENTS

JP 2001-311686 A 11/2001
JP 2003-014716 A 1/2003
(Continued)

OTHER PUBLICATIONS

MIDAC corporation PFC Monitoring by FTIR in LCD industry, Analysis background knowledge—Application example of analysis equipment/Application example of ft-ir gas analysis [searched on Feb. 13, 2018], Internet <URL: https://www.kdijpn.co.jp/>.
(Continued)

*Primary Examiner* — Jamil Ahmed
(74) *Attorney, Agent, or Firm* — Volpe Koenig

(57) ABSTRACT

Provided are a method and a device that do not require any pretreatment and measure and analyze impurities or hydrogen fluoride in corrosive gas with high sensitivity. The method and the device measure a fluorine-based gas in a sample containing a corrosive gas with a Fourier transform infrared spectrophotometer, wherein the Fourier transform infrared spectrophotometer includes a detector having an InGaAs detection element and a single-path gas cell having an optical path length of 0.01 m to 2 m, a cell window is made of a corrosion-resistant material, a measurement region ranges from 3800 to 14300 $cm^{-1}$ in wavenumber, and the concentration of the fluorine-based gas is quantified based on an amount of absorption of light having a predetermined wavenumber by the sample and a calibration curve.

7 Claims, 4 Drawing Sheets

(56) References Cited

U.S. PATENT DOCUMENTS

| | | | |
|---|---|---|---|
| 2004/0184980 A1* | 9/2004 | Atobe | H01L 31/1804 423/342 |
| 2006/0241491 A1* | 10/2006 | Bosch-Charpenay | G01J 3/45 600/473 |
| 2008/0279726 A1 | 11/2008 | Kaufmann et al. | |
| 2012/0185179 A1* | 7/2012 | Zhou | G01N 21/3504 702/24 |
| 2014/0183362 A1 | 7/2014 | Islam | |
| 2016/0003676 A1* | 1/2016 | Fukuda | G01J 3/0275 250/339.08 |

FOREIGN PATENT DOCUMENTS

| | | |
|---|---|---|
| JP | 2003-095636 A | 4/2003 |
| JP | 2008-197120 A | 8/2008 |
| JP | 2008-532052 A | 8/2008 |
| JP | 2008-214187 A | 9/2008 |
| JP | 2008-275650 A | 11/2008 |

OTHER PUBLICATIONS

Tooke, P., et al., "Resolution, Apodisation and Bandshape in FTIR Sepctroscopy," SPIE, vol. 1145, Fourier Transform Spectroscopy (1989), 3 pgs.

Extended European Search Report dated Oct. 20, 2021 for European Patent Application No. 19768083.8.

Lowry et al., "Determination of Wavelength Accuracy in the Near-Infrared Spectral Region Based on NIST's Infrared Transmission Wavelength Standard SRM 1921," vol. 54 issue: 3, pp. 450-455 (Mar. 1, 2000).

\* cited by examiner

METHOD AND DEVICE FOR ANALYZING GAS

TECHNICAL FIELD

The present invention relates to a method and a device for measuring and analyzing impurities or hydrogen fluoride (which may hereinafter be abbreviated as HF) in a corrosive gas. More specifically, the present invention relates to a method and a device for qualitatively or quantitatively measuring and analyzing impurities or hydrogen fluoride contained in a corrosive gas containing halogen atoms.

BACKGROUND ART

Compounds having corrosiveness which contain halogen atoms in compositions thereof are often used as a gas for electronic materials in semiconductor manufacturing or the like. Since it is known that impurities in gas greatly affect the characteristics of devices and also affect semiconductor manufacturing apparatuses, it is preferable that the concentration of the impurities is as low as possible. For example, it is described in paragraph [0005] of Background Art of Patent Document 1 that hydrogen fluoride contained as impurities in gas is required to be removed so that the concentration thereof is reduced as close to null as possible, for the purpose of use in a semiconductor manufacturing process.

Conventionally, a trace of impurities contained in a gas sample, for example, impurities of only 1 ppm or less contained in a gas sample has been quantitatively measured and analyzed with a Fourier transform infrared spectrophotometer (which may hereinafter be abbreviated as FT-IR) equipped with an MCT or TGS detector, and a multi-reflection long optical path gas cell (multipath gas cell) having an optical path length of 1 m to 20 m in which a reflecting mirror is provided in an optical path in order to enhance light absorption sensitivity. For example, Patent Document 2 describes a method of measuring a fluorine-based gas component with a Fourier transform infrared spectrophotometer, and describes that hydrogen fluoride can be measured at around 4000 $cm^{-1}$ (Table 1).

However, in the method of performing measurement and analysis by using the multi-reflection long optical path gas cell having the reflecting mirror in the optical path, when a corrosive gas sample is made to flow through the multi-reflection long optical path gas cell, there is a problem that the reflecting mirror for increasing the optical path length set in the optical path inside the gas cell is corroded and deteriorated, resulting in deterioration of sensitivity, and eventually the gas cell becomes unusable. In the method of Patent Document 2, the detection concentration of hydrogen fluoride is several tens to several thousand ppm, which is not a method having high sensitivity of 1 ppm or less. Non-Patent Document 1 describes that the detection limit of hydrogen fluoride is 12.5 ppm when a single-path 10 cm gas cell is used.

In addition to the above-described methods, as a method of analyzing a trace component using no multi-reflection long optical path gas cell is known a method of removing corrosive gas components, and when an impurity component has a low concentration, further condensing and measuring a trace component. For example, Patent Document 3 describes that for measurement of hydrogen fluoride in fluorine gas, $F_2$ gas is fixed and removed and the measurement is performed by using a 1.5 m gas cell.

However, this method requires pretreatments such as removal of corrosive gas components and, in some cases, a condensing operation of impurity components before measurement of a sample. For this reason, there have been problems that many steps are required for measurement and analysis, and errors are increased due to the pretreatments.

Further, a method in which no reflecting mirror is put inside a gas cell to increase a tube length of the gas cell and measurement is performed with a so-called single-path optical path length is considered as a method of increasing the optical path length with no multi-reflection long optical path gas cell and enhancing the measurement accuracy and sensitivity. However, in this method, when the cell length is 1 m or more, the internal volume of the cell increases to cause deterioration in gas purging performance, and increase of the tube length of the gas cell causes problems that light attenuation increases, the device space increases, the weight increases, etc. Therefore, this method is not suitable for practical use.

Therefore, there have been required a method and a device that solve the above-described problems, do not require any pretreatment, and measure and analyze impurities, particularly hydrogen fluoride, in a corrosive gas with high sensitivity.

PRIOR ART DOCUMENT

Patent Document

Patent Document 1: Japanese Patent Laid-Open No. 2008-214187

Patent Document 2: Japanese Patent Laid-Open No. 2008-197120 (Table 1)

Patent Document 3: Japanese Patent Laid-Open No. 2003-014716

Non-Patent Document

Non-Patent Document 1: MIDAC corporation PFC Monitoring by FTIR in LCD industry, Analysis background knowledge—Application example of analysis equipment/ Application example of ft-ir gas analysis [searched on Feb. 13, 2018], Internet <URL: https://www.kdijpn.co.jp/>

SUMMARY OF THE INVENTION

Problems to be Solved by the Invention

An object of the present invention is to solve such problems and provide a method and a device for measuring and analyzing impurities or hydrogen fluoride in a corrosive gas with high sensitivity without requiring a pretreatment. More specifically, there are provided a method and a device that can be reduced in labor because a pretreatment is unnecessary, and can measure an accurate concentration with high sensitivity when measuring the concentration of hydrogen fluoride in a measurement target gas containing a corrosive gas discharged from a gas manufacturing process and various other manufacturing processes of an electronic device manufacturing apparatus, etc.

Means for Solving the Problems

The present inventor has conducted intensive studies to solve the above-described problems, and has found that when a fluorine-based gas in a sample containing a corrosive gas is measured with a Fourier transform infrared spectrophotometer, a fluorine-based gas such as hydrogen fluoride in the presence of a corrosive gas can be quantitatively analyzed with high sensitivity without requiring any pretreatment by using a single-path gas cell having no reflecting mirror in the optical path to prevent corrosion even in the presence of the corrosive gas and further using an InGaAs detector to enhance sensitivity.

In particular, it has surprisingly been found that the single-path gas cell having no reflecting mirror in the optical path can measure the fluorine-based gas with high sensitivity despite its short optical path length. Furthermore, it has been found that the fluorine-based gas can be quantitatively measured precisely by measuring the fluorine-based gas such as hydrogen fluoride as a measurement target in a measurement wavenumber region in which water ($H_2O$) mixed in the sample and in the device does not hinder the measurement, and finally the present invention has been completed.

In other words, the present invention relates to a gas analyzing method for measuring a fluorine-based gas in a sample containing a corrosive gas with a Fourier transform infrared spectrophotometer, wherein the Fourier transform infrared spectrometer comprises a detector having an InGaAs detection element and a single-path gas cell having an optical path length of 0.01 m to 2 m, a cell window is made of a corrosion-resistant material, a measurement region ranges from 3800 to 14300 $cm^{-1}$ in wavenumber, and a concentration of the fluorine-based gas is quantified based on an amount of absorption of light having a predetermined wavenumber by the sample and a calibration curve.

Furthermore, the present invention relates to the above method in which the corrosive gas is a compound to be hydrolyzed in an atmosphere such as fluorine, krypton difluoride, xenon difluoride, xenon tetrafluoride, xenon hexafluoride, chlorine monofluoride, chlorine trifluoride, chlorine pentafluoride, bromine monofluoride, bromine trifluoride, bromine pentafluoride, iodine monofluoride, iodine trifluoride, iodine pentafluoride, iodine heptafluoride, silicon tetrafluoride, boron trifluoride, diboron tetrafluoride, arsenic trifluoride, phosphorus trifluoride, phosphorus pentafluoride, oxygen difluoride, dioxygen difluoride, germanium tetrafluoride, sulfur tetrafluoride, vanadium pentafluoride, molybdenum hexafluoride, uranium hexafluoride, rhenium hexafluoride, rhenium heptafluoride, osmium hexafluoride, iridium hexafluoride, platinum hexafluoride, tungsten hexafluoride, nitrosyl monofluoride, nitrosyl trifluoride, carbonyl fluoride, monofluoromethyl hypofluoride, methyl hypofluoride, difluoromethyl hypofluoride, trifluoromethyl hypofluoride, acetylfluoride, monofluoroacetylfluoride, difluoroacetylfluoride, trifluoroacetylfluoride, oxalic acid monofluoride, oxalic acid difluoride or the like.

The fluorine-based gas is preferably hydrogen fluoride.

The present invention relates to the above method in which a cell window is made of a corrosion-resistant material. For example, one kind selected from the group consisting of $CaF_2$, $BaF_2$, $MgF_2$, LiF and ZnSe can be used, and among them, $CaF_2$ is preferable.

The present invention relates to the above method in which the measurement region ranges from 3950 to 4200 $cm^{-1}$ in wavenumber.

The present invention relates to a gas analyzing device comprising a Fourier transform infrared spectrophotometer for measuring a fluorine-based gas in a sample containing a corrosive gas, the Fourier transform infrared spectrophotometer including a light source, a beam splitter, a fixed mirror, a movable mirror, a measurement cell, a detector, and an information processing device, the detector includes a detector having an InGaAs detection element, the measurement cell is provided with a sample gas inlet and a sample gas outlet, and includes a single-path gas cell having an optical path length of 0.01 m to 2 m, a cell window in the measurement cell is made of a corrosion-resistant material, an interference mechanism is provided that includes the beam splitter, the fixed mirror, and the movable mirror so that light emitted from the light source is controlled to have a wavenumber range of 3800 to 14300 $cm^{-1}$ and impinges onto a sample, and the information processing device is configured to quantify a concentration of the fluorine-based gas from an amount of absorption of light having a predetermined wavenumber by the sample and a preset calibration curve.

The present invention relates to the above-described device in which the corrosive gas is tungsten hexafluoride, and the fluorine-based gas is hydrogen fluoride.

The present invention relates to the above-described device in which the cell window is made of a corrosion-resistant material. For example, one kind selected from the group consisting of $CaF_2$, $BaF_2$, $MgF_2$, LiF and ZnSe can be used, and among them, $CaF_2$ is preferable.

The present invention relates to the above-described device in which light emitted from the light source is controlled to have a wavenumber range of 3950 to 4200 $cm^{-1}$ and impinges onto the sample.

The present invention relates to the above-described device in which when a spectrum based on an absorption amount detected by the detector is subjected to Fourier transform in the information processing device, Trapezium is used as an apodization function.

Hereinafter, the present invention will be described in detail with reference to the drawings as appropriate.

A gas analyzing method and a gas analyzing device of the present invention are a method for measuring a fluorine-based gas in a sample containing a corrosive gas with a Fourier transform infrared spectrophotometer, and a device for the method.

FIG. 1 shows a configuration of a Fourier transform infrared spectrophotometer 1 used in the present invention. In FIG. 1, a light source 2 configured to emit parallel light, an interference mechanism for interfering with and outputting light (normally, infrared light) from the light source 2, a measurement cell 6 which accommodates a sample or the like therein and is irradiated with light from the light source 2 via the interference mechanism, and a detector 7 for receiving light passing through the measurement cell 6. The interference mechanism includes a fixed mirror 5, a beam splitter 3, and a movable mirror 4 that is caused to translate, for example, in XY directions by a driving mechanism (not shown).

An information processing device 8 is a general-purpose or dedicated computer including a CPU, a memory, an input/output interface, an AD converter, and the like, and causes the CPU, peripheral devices, and the like to cooperate with one another according to a predetermined program stored in a predetermined area of the memory, whereby information processing and printing on a printer can be performed.

In the present invention, as a mode of information processing in the information processing device 8, an absorption spectrum of a measurement target object, for example, hydrogen fluoride in a measurement sample which is detected by the detector 7 is compared with a baseline which was measured in a background including only an inert gas such as nitrogen, and subjected to Fourier transform to perform information processing. When Fourier transform is performed in the information processing device 8, it is preferable to use Trapezium as an apodization function.

In FIG. 4, baseline waveforms based on different apodization functions for the same baseline were traced. In FIG. 4, the horizontal axis (X axis) represents the wavenumber (unit: $cm^{-1}$), and the vertical axis (Y axis) represents the absorbance. In FIG. 4, as can be seen from the baselines obtained by using respective functions of Triangle (32), Trapezium (31), and Cosine (33), use of Trapezium (31) makes peaks, for example, peaks of the absorption spectrum of hydrogen fluoride sharper than the other functions, that is, makes the intensity of the peaks higher, which makes it apparent that Trapezium (31) is also suitable for quantification of the fluorine-based gas.

In the measurement using the Fourier transform infrared spectrophotometer 1, as a method of checking a peak attributed to hydrogen fluoride, a spectrum of a standard gas of hydrogen fluoride is compared, and when there is a peak having the same shape at the same wavenumber, the peak is identified as the peak of hydrogen fluoride. As a numerical data generation method for the peak, a "peak height" program on software used in the information processing device 8 is used, and a calculation can be made by specifying "a peak attributed to hydrogen fluoride" and "noise peaks other than the peak of hydrogen fluoride". Peaks at positions adjacent to the peak attributed to hydrogen fluoride are noises. "Noise peak height" may be calculated from the apex and base of each of the nearest right and left noise peaks to the peak attributed to hydrogen fluoride, and the signal/noise ratio (S/N ratio) may also be calculated as "height ratio".

FIG. 5 shows a spectrum of a standard gas obtained by diluting hydrogen fluoride with nitrogen (the concentration of hydrogen fluoride is 13.4 ppm). An upper part of FIG. 5 shows a result when a detector having an InGaAs detection element is used under a condition of 50 times integration, and a lower part shows a result when a detector having an MCT detection element is used under a condition of 128 times integration. The horizontal axis (X axis) represents the wavenumber (unit: $cm^{-1}$), and the vertical axis (Y axis) represents the absorbance. Although the detection elements are different, it is recognized that the absorption spectrum of hydrogen fluoride has a plurality of peaks in the wavenumber range of 3550 to 4300 $cm^{-1}$ as also recognized in FIG. 2. For this reason, it is preferable that the wavenumber of 4075 $cm^{-1}$ providing the highest peak is selected to quantify hydrogen fluoride, and used for quantification. Note that FIG. 2 shows absorption spectrum data obtained by the Fourier transform infrared spectrometer, which are data of "Transactions of the Japan Society of Mechanical Engineers: B edition, volume 70 (2004) 692, p1058-1063".

This wavenumber selection may be applied in a case where water may be mixed in the sample and hydrogen fluoride is quantified. Therefore, when the impurity components other than water have absorption in the wavenumber range of 3550 to 4300 $cm^{-1}$ or when a fluorine-based gas other than hydrogen fluoride is measured, a wavenumber or a wavenumber range where quantification is performed may be selected appropriately.

FIG. 6 is a calibration curve obtained by using a standard gas in which hydrogen fluoride is diluted with nitrogen. The horizontal axis (X axis) represents the concentration of hydrogen fluoride, which indicates each concentration of 0.47 to 4.71 ppm. The absorption amounts at the wavenumber of 4075 $cm^{-1}$ obtained for these concentrations of hydrogen fluoride obtained by using the Fourier transform infrared spectrometer according to the present invention are indicated as the absorbance on the vertical axis (Y axis). The concentration of hydrogen fluoride can be calculated by obtaining the absorbance of unknown concentration of hydrogen fluoride in the sample using this calibration curve. In other words, the concentration of the fluorine-based gas can be quantified from the absorption amount in the measurement sample and the preset calibration curve by light having a predetermined wavenumber.

In the measurement of the concentration of hydrogen fluoride based on this calibration curve, if the data of the calibration curve is input to the information processing device 8 in FIG. 1 in advance, the concentration of hydrogen fluoride can be calculated from the absorbance obtained by the sample measurement. Note that, as a method of preparing a calibration curve, it is possible to simply connect points indicating the concentrations of the hydrogen fluoride and absorbances, for example, points indicated by black circles in FIG. 6 with a straight line, or perform a linear regression using the least squares method or the like, or it is also possible to adopt a general-purpose method that uses a quadratic function or a higher-order function so as to enhance fitting. Furthermore, it is also possible to weight a concentration region in which the concentration of a measurement target object and the absorbance thereof are excellently correlated with each other, for example, by weighting numerical values or the like.

The Fourier transform infrared spectrophotometer used in the present invention essentially requires the use of a detector having a highly sensitive InGaAs detection element. As described in examples described below, when a detector having an MCT detection element or a TGS detection element is used, the detection sensitivity (quantifiable concentration) is insufficient, and therefore it is important to use a Fourier transform infrared spectrophotometer including a detector having an InGaAs detection element that can be made higher in sensitivity.

A single-path gas cell having an optical path length of 0.01 m to 2 m is preferably used as the gas cell provided in the Fourier transform infrared spectrophotometer. More preferably, the optical path length may be set to 0.1 m to 1 m. The optical path length may be appropriately determined so that the optical path length can be measurably set to an appropriate length according to the amount or concentration of a measurement target contained in the corrosive gas. Usually, the optical path length can be determined in consideration of the size of the spectrophotometer, a place where the measurement is performed, and the like.

Here, in the present invention, a single-path gas cell having an optical path length of 0.01 m to 2 m is used as the gas cell provided in the Fourier transform infrared spectrophotometer because in a long optical path gas cell having a reflecting mirror in a gas cell, the reflecting mirror is corroded by a corrosive gas, which makes it impossible to perform proper measurement.

FIG. 3A is a schematic diagram of a long optical path gas cell 10, and FIG. 3B is a schematic diagram of a single-path gas cell 20.

In the long optical path gas cell 10, light incident through a reflecting mirror 11 is reflected at plural times by the reflecting mirror 11 as indicated by arrows, during which the light is absorbed by a measurement target compound in a gas cell 12, whereby the light absorption amount can be increased or amplified until the light is received by the detector. The detection sensitivity is enhanced by such a mechanism. However, when a corrosive gas, for example, a halogen-based gas such as tungsten hexafluoride exists in the gas cell, the corrosive action of the corrosive gas corrodes the reflecting mirror, and the reflecting mirror cannot function properly, so that enhancement of the measurement sensitivity is unexpectable.

On the other hand, in the single-path gas cell 20, there is no reflecting mirror in a gas cell 21. In the measurement of a sample, the measurement sample is introduced into the gas cell 21 via a gas inlet 22 (or 23), and after the measurement, the sample is discharged via a gas outlet 23 (or 22). The measurement sample stays in the gas cell and absorbs incoming light, and the light is only received by the detector. In other words, the single-path gas cell 20 suffers only light absorption through the single path because no reflecting mirror exists in the gas cell 21. Therefore, since it is impossible to increase or amplify the amount of light absorption by the measurement target object as in the case of the long optical path gas cell, it is necessary to enhance the sensitivity of the detector, and thus it is significant in the present invention to use a detector having a highly sensitive InGaAs detection element.

The single-path gas cell 20 shown in FIG. 3B has a cylindrical shape, and is provided with cell windows (not shown) for infrared light at both ends thereof. The Fourier transform infrared spectrophotometer 1 (FIG. 1) causes a sample containing a corrosive gas to flow into the single-path gas cell 20 and measures a light attenuation amount of infrared light passing through the single-path gas cell 20 to measure the concentration of a fluorine-based gas in the sample gas. It is preferable that the cell window (not shown) for transmitting infrared light therethrough into the gas cell is made of a corrosion-resistant material such as calcium fluoride ($CaF_2$) which is not corroded by the corrosive gas as in the case described with reference to the reflection mirror.

Note that, with respect to the single-path gas cell 20 of FIG. 3B, a sample containing a corrosive gas may be directly introduced into the single-path gas cell 20 via the gas inlet 22 (or 23) from a manufacturing process or various processes and used for process analysis.

Further, a heater (not shown) such as a band heater or a cooler (not shown) may be attached to an outer peripheral portion of the single-path gas cell 20 so that the gas inside the single-path gas cell 20 is maintained at a certain set temperature.

In the present invention, the measurement region is in a wavenumber range of 3800 to 14300 $cm^{-1}$, and preferably in the wavenumber range of 3950 to 4200 $cm^{-1}$. However, in FIG. 1, the wavenumber of light generated by the interference mechanism including the beam splitter 3, the fixed mirror 5 and the movable mirror 4 from the light source 1 may be any wavenumber as long as the installed interference mechanism allows it. Usually, the wavenumber may be any wavenumber used in a Fourier transform infrared spectrophotometer. Therefore, the measurement region described here means a region that can cover wavenumbers at which a substance or compound as a measurement target can absorb light in the present invention.

For example, in the case of hydrogen fluoride, as recognized in FIG. 2, the wavenumber may be in the wavenumber range of 3950 to 4200 $cm^{-1}$. The reason for this is that when water is mixed in the measurement sample, absorption is observed in a wavenumber range of 3600 to 3950 $cm^{-1}$ which is near to the absorption wavenumber of hydrogen fluoride, and there is a concern that the measurement of hydrogen fluoride is hindered.

In the present invention, when a fluorine-based gas other than hydrogen fluoride in a sample containing a corrosive gas is measured, it is preferable to set the wavenumber of light to be used for appropriate measurement in consideration of each component contained in a sample as a measurement target.

Advantageous Effect of the Invention

According to the present invention, it is possible to provide a method that does not require any pretreatment, and measures and analyzes impurities or hydrogen fluoride in a corrosive gas with high sensitivity.

According to the present invention, it is possible to provide a device for analyzing a fluorine-based gas which does not require any pretreatment, has high sensitivity, and is hardly affected by a corrosive gas.

EXAMPLES

Hereinafter, the present invention will be described in more detail with reference to Examples, but the scope of the present invention is not limited to the following Examples.

Example 1

Figure 1:
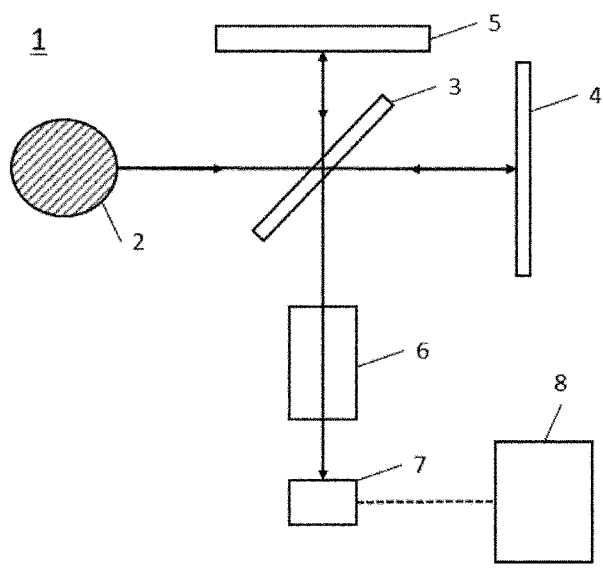
FIG. 1 is a diagram showing a schematic configuration of a Fourier transform infrared spectrophotometer in a gas analyzing device according to an embodiment of the present invention.
Figure 2:
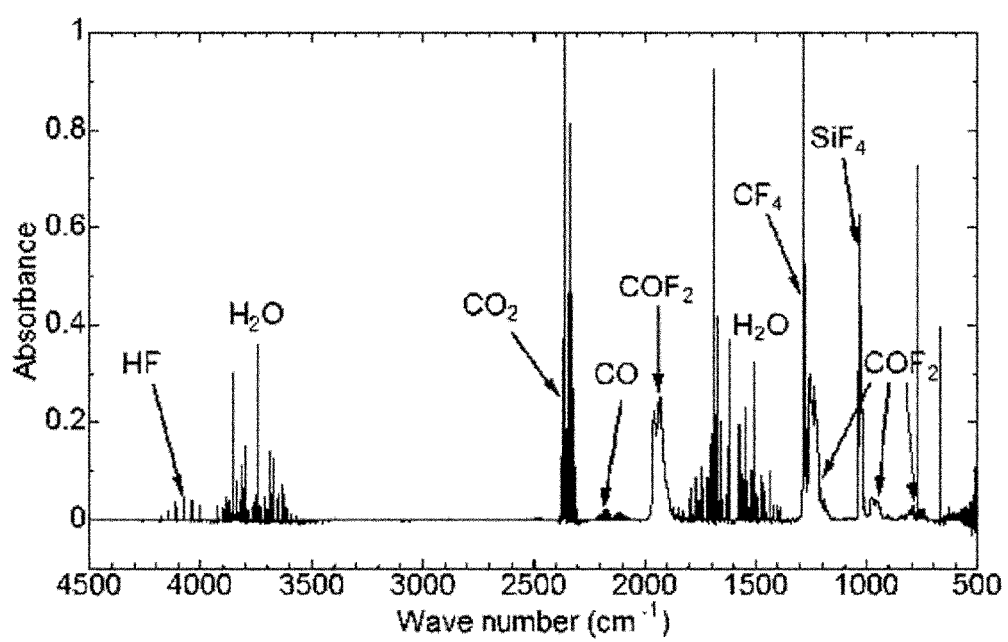
FIG. 2 shows absorption spectrum data of various compounds measured by a Fourier transform infrared spectrophotometer.
Figure 3A:
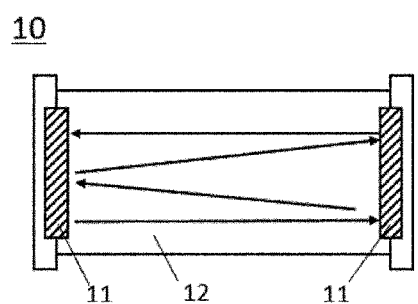
FIG. 3A is a diagram showing a schematic configuration of a multi-reflection long optical path gas cell in the Fourier transform infrared spectrophotometer.
Figure 3B:
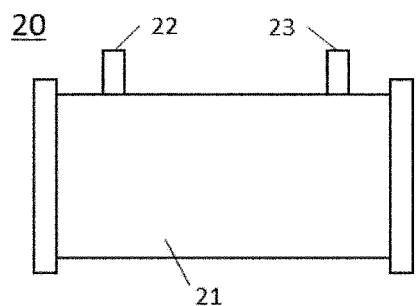
FIG. 3B is a diagram showing a schematic configuration of a single-path gas cell in the Fourier transform infrared spectrophotometer.
Figure 4:
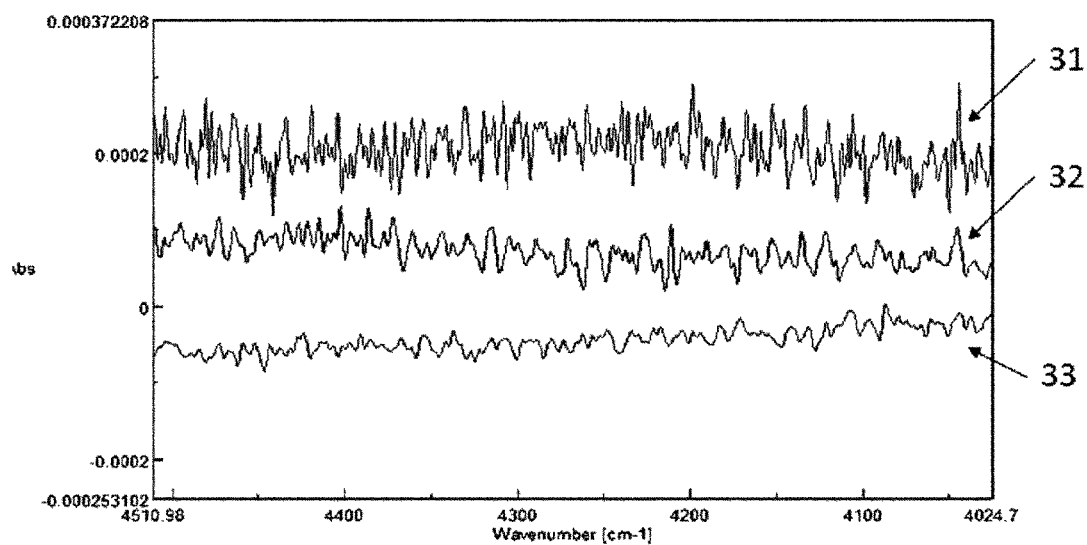
FIG. 4 shows traces of baseline waveforms based on different apodization functions for the same baseline with respect to the absorption spectrum data obtained by the Fourier transform infrared spectrophotometer.

A Fourier transform infrared spectrophotometer had the configuration shown in FIG. 1, and a detector having an InGaAs detection element was used as the detector. The measurement was performed by using, as the gas cell, a single-path short optical path gas cell having a length of 0.10 m (10 cm) and having no reflecting mirror.

A material made of calcium fluoride ($CaF_2$) was used for the cell window of the single-path gas cell. The resolution was set at 2 $cm^{-1}$, the number of times of integration was set to 50 times, the measurement region was set at 3,950 $cm^{-1}$ to 4,200 $cm^{-1}$, and the apodization function was set to Trapezium. Other conditions were set based on the specification and description of the device used.

A hydrogen fluoride standard gas of 0.39 ppm to 23.29 ppm was adjusted by using a permeator as a calibration gas preparation device, a permeation tube for hydrogen fluoride, and nitrogen for dilution to measure a measurement target.

Figure 5:
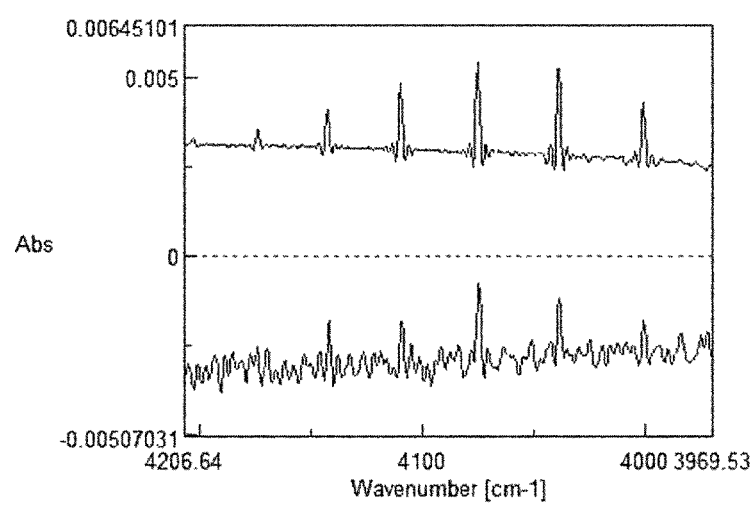
FIG. 5 is a spectrum of a standard gas (the concentration of hydrogen fluoride is 13.4 ppm) obtained by diluting hydrogen fluoride with nitrogen.
Figure 6:
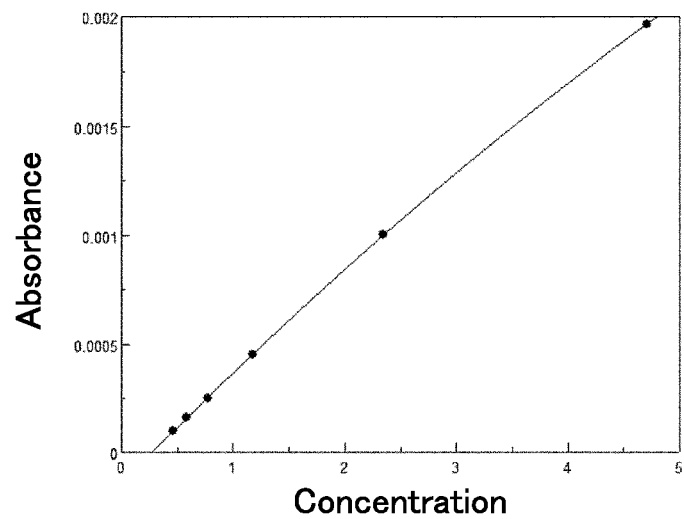
FIG. 6 is a calibration curve obtained by using a standard gas obtained by diluting hydrogen fluoride with nitrogen.

As can be seen from FIG. 5, calibration curves of a linear equation and a quadratic equation based on the least squares method were prepared by using the peak of hydrogen fluoride appearing at 4075 cm$^{-1}$ from the spectrum of the hydrogen fluoride standard gas of each concentration. As a result of preparing the calibration curves, a strong correlation was obtained with the determination coefficient $R^2=0.99$ or more in all cases in the range of the hydrogen fluoride concentration of 0.47 ppm or more. FIG. 6 shows a part of the prepared calibration curve which was prepared in the range of 0.47 ppm to 4.71 ppm in hydrogen fluoride concentration.

Comparative Example 1

The detector was changed from a detector having an InGaAs detection element of Example 1 to a detector having an MCT detection element and a TGS detection element, and the hydrogen fluoride standard gas was measured as in the case of Example 1.

Example 2

The ratio of the peak of hydrogen fluoride appearing at 4075 cm$^{-1}$ to the average of right and left noises most adjacent to the peak of hydrogen fluoride appearing at 4075 cm$^{-1}$ (hereinafter referred to as "S/N ratio") was determined from the hydrogen fluoride spectra of the hydrogen fluoride standard gases obtained in Example 1 and Comparative Example 1, and it is shown in Table 1.

TABLE 1

| Concentration of hydrogen fluoride standard gas | S/N ratio by InGaAs detection element (integration of 50 times) | S/N ratio by MCT detection element (integration of 128 times) | S/N ratio by TGS detection element (integration of 128 times) |
| --- | --- | --- | --- |
| 26.79 ppm | | 7.54 | 8.86 |
| 23.29 ppm | 5.92 | | |
| 13.40 ppm | 6.05 | 5.13 | 8.01 |
| 6.70 ppm | 6.34 | 4.45 | 3.14 |
| 4.71 ppm | 6.02 | 3.76 | 1.59 |
| 2.35 ppm | 5.59 | 0.76 | — |
| 1.13 ppm | 5.19 | — | — |
| 0.78 ppm | 5.81 | — | — |
| 0.59 ppm | 4.35 | — | — |
| 0.47 ppm | 4.98 | — | — |
| 0.39 ppm | 2.82 | — | — |

In Table 1, the S/N ratio can be improved in accuracy by increasing the number of times of integration in a Fourier transform step, but the measurement time is longer as the number of times increases. The following Table 2 shows the relationship between the number of times of integration and the measurement time when the Fourier transform infrared spectrophotometer was used.

TABLE 2

| | InGaAs detection element | MCT detection element | TGS detection element |
| --- | --- | --- | --- |
| Integration of 128 times | 2 minutes and 8 seconds | 1 minute and 58 seconds | 3 minutes and 48 seconds |
| Integration of 64 times | 1 minute and 8 seconds | 59 seconds | 1 minute and 52 seconds |
| Integration of 50 times | 49 seconds | 46 seconds | 1 minute and 28 seconds |

As can be seen from Tables 1 and 2, by increasing the number of times of integration, the S/N ratio is improved, but more measurement time is required. For this reason, when efficient or quick measurement is required in process analysis or the like, it is necessary to avoid the number of times of integration from increasing more than necessary. Therefore, it can be understood that the use of the detector having the InGaAs detection element improves the measurement sensitivity and also enables quick measurement. In other words, it was confirmed that the detector having the InGaAs detection element had less noise and was able to analyze a trace concentration more than the detector having the MCT detection element and the TGS detection element.

In the above Table 1, a measurement result obtained by using the detector having the InGaAs detection element is shown as a calibration curve in FIG. 6. As described above, a highly accurate calibration curve having a determination coefficient $R^2=0.99$ or more could be obtained.

From Table 1, a hydrogen fluoride standard gas was measured in combination of a Fourier transform infrared spectrophotometer having an InGaAs detector installed therein and a 0.10 m (10 cm) gas cell having no reflecting mirror therein, and as a result, quantitativity was observed up to 0.5 ppm for the hydrogen fluoride concentration. From this, it is estimated that it is possible to quantify up to 0.05 ppm when a 1.0 m gas cell is used for measurement.

From Table 1, as a comparative example, the gas cell used in Example 1 was used, the detector having the InGaAs detection element was changed to the detector having the MCT and TGS detection elements, the number of times of integration was changed to 128 which was 2.56 times of that in Example 1, and the hydrogen fluoride standard gas was measured. As a result, the lower limit of quantification of hydrogen fluoride was 6 to 7 ppm.

Example 3

By using the calibration curve obtained in Example 2, a corrosive gas (tungsten hexafluoride) containing hydrogen fluoride was measured.

Figure 7:
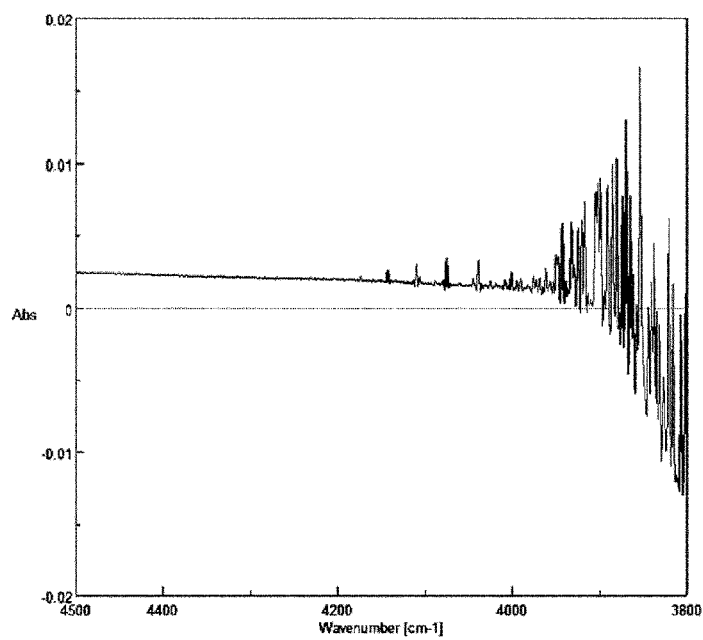
FIG. 7 is a diagram showing a spectrum of hydrogen fluoride in tungsten hexafluoride in Example 3.

FIG. 7 is a diagram showing the spectrum of hydrogen fluoride in tungsten hexafluoride. The horizontal axis (X axis) represents the wavenumber (unit: cm$^{-1}$), and the vertical axis (Y axis) represents the absorbance. Among these, the concentration of hydrogen fluoride was determined based on the wavenumber of 4047 cm$^{-1}$ which provided a highest peak of hydrogen fluoride, and it was 5.1 ppm.

As described above, it was possible to quantify a trace of impurities such as hydrogen fluoride of 1 ppm or less in a gas sample containing a corrosive component without a multi-reflection long optical path gas cell having a reflecting mirror therein. Since no reflecting mirror is used inside the gas cell, the durability of the analyzing device and the stability of the measurement (the influence of noise is small and reproducibility is excellent) are also enhanced. Further, no pretreatment is required.

INDUSTRIAL APPLICABILITY

According to the present invention, a method and a device can be provided which measure and analyze the impurities, hydrogen fluoride or the like in a corrosive gas containing halogen atoms.

EXPLANATION OF REFERENCE SIGNS

1 Fourier transform infrared spectrometer
2 light source
3 beam splitter
4 movable mirror
5 fixed mirror
6 measurement cell
7 detector
8 information processing device
10 multi-reflection long optical path gas cell
11 reflecting mirror
12 gas cell
20 single-path gas cell
21 gas cell
22, 23 gas inlet or outlet

The invention claimed is:

1. A gas analyzing method for measuring hydrogen fluoride in a sample containing a corrosive gas and water with a Fourier transform infrared spectrophotometer, wherein
the Fourier transform infrared spectrophotometer comprises a detector having an InGaAs detection element and a single-path gas cell having an optical path length of 0.01 m to 2 m,
a cell window is made of a corrosion-resistant material, a measurement region ranges from 3800 to 14300 $cm^{-1}$ in wavenumber, and
a concentration of hydrogen fluoride is quantified based on an amount of absorption of light having a predetermined wavenumber by the sample and a calibration curve.

2. The method according to claim 1, wherein the cell window is made of one kind selected from the group consisting of $CaF_2$, $BaF_2$, $MgF_2$, LiF and ZnSe.

3. The method according to claim 1, wherein the measurement region ranges from 3950 to 4200 $cm^{-1}$ in wavenumber.

4. A gas analyzing device comprising a Fourier transform infrared spectrophotometer for measuring hydrogen fluoride in a sample containing a corrosive gas and water,
the Fourier transform infrared spectrophotometer including a light source, a beam splitter, a fixed mirror, a movable mirror, a measurement cell, a detector, and an information processing device,
the detector includes a detector having an InGaAs detection element,
the measurement cell is provided with a sample gas inlet and a sample gas outlet, and includes a single-path gas cell having an optical path length of 0.01 m to 2 m,
a cell window in the measurement cell is made of a corrosion-resistant material,
an interference mechanism is provided that includes the beam splitter, the fixed mirror, and the movable mirror so that light emitted from the light source is controlled to have a wavenumber range of 3800 to 14300 $cm^{-1}$ and impinges onto a sample, and
the information processing device is configured to quantify a concentration of hydrogen fluoride from an amount of absorption of light having a predetermined wavenumber by the sample and a preset calibration curve.

5. The device according to claim 4, wherein the cell window is made of one kind selected from the group consisting of $CaF_2$, $BaF_2$, $MgF_2$, LiF and ZnSe.

6. The device according to claim 4, wherein light emitted from the light source is controlled to have a wavenumber range of 3950 to 4200 $cm^{-1}$ and impinges onto the sample.

7. The device according to claim 4, wherein when a spectrum based on an absorption amount detected by the detector is subjected to Fourier transform in the information processing device, Trapezium is used as an apodization function.

* * * * *